United States Patent [19]

Hillebrand et al.

[11] Patent Number: 5,645,825
[45] Date of Patent: Jul. 8, 1997

[54] DEPILATORY COMPOSITIONS COMPRISING SULFHYDRYL COMPOUNDS

[75] Inventors: Greg George Hillebrand, Fairfield; Vladimir Gartstein, Cincinnati, both of Ohio

[73] Assignee: The Procter & Gamble Company, Cincinnati, Ohio

[21] Appl. No.: 479,878

[22] Filed: Jun. 7, 1995

[51] Int. Cl.$^6$ .............................. A61K 7/15; A61K 7/06; A61K 31/095
[52] U.S. Cl. ................ 424/73; 424/70.2; 424/70.5; 424/70.51; 514/706; 514/707
[58] Field of Search .................. 424/73, 70.2, 70.5, 424/70.51; 514/2, 706, 707

[56] References Cited

U.S. PATENT DOCUMENTS

| | | |
|---|---|---|
| 3,242,052 | 3/1966 | Sheffner . |
| 3,865,546 | 2/1975 | Zemlin et al. . |
| 4,195,095 | 3/1980 | Sheffner ................... 424/317 |
| 4,411,886 | 10/1983 | Hostettler et al. ............ 424/70 |
| 4,919,924 | 4/1990 | Pigiet ....................... 424/72 |
| 4,935,231 | 6/1990 | Pigiet ....................... 424/71 |
| 5,095,007 | 3/1992 | Ahluwalia ................. 514/23 |
| 5,296,500 | 3/1994 | Hillebrand ................ 514/476 |
| 5,362,748 | 11/1994 | Schwen et al. ........... 514/476 |
| 5,411,991 | 5/1995 | Shander et al. ........... 514/665 |

FOREIGN PATENT DOCUMENTS

| | | |
|---|---|---|
| 0287773 | 10/1988 | European Pat. Off. . |
| 0302265 | 2/1989 | European Pat. Off. . |
| 585018 | 3/1994 | European Pat. Off. . |
| 2347040 | 11/1977 | France . |
| 4206692A1 | 9/1993 | Germany . |
| 53-130442 | 11/1978 | Japan . |
| 57-16810 | 1/1982 | Japan . |
| 58-183614 | 10/1983 | Japan . |
| 61-165316 | 7/1986 | Japan . |
| 64-9919 | 1/1989 | Japan . |
| 6-157257 | 11/1992 | Japan . |
| 5-39211 | 2/1993 | Japan . |
| 06092833 | 4/1994 | Japan . |
| 6135825 | 5/1994 | Japan . |
| 518717 | 3/1972 | Switzerland . |
| 636181 | 4/1950 | United Kingdom . |
| 649329 | 1/1951 | United Kingdom . |
| WO91/10421 | 7/1991 | WIPO . |
| WO93/10755 | 6/1993 | WIPO . |
| WO94/05255 | 3/1994 | WIPO . |
| WO94/05279 | 3/1994 | WIPO . |
| WO94/05302 | 3/1994 | WIPO . |
| WO94/04128 | 3/1994 | WIPO . |
| WO94/04129 | 3/1994 | WIPO . |
| WO94/14428 | 7/1994 | WIPO . |

OTHER PUBLICATIONS

3–Patch Human Skin Irritation Test; the Procter & Gamble Co.; Jun., 1992.

Human Skin Sensitization Study; the Procter & Gamble Co.; Jul., 1992–May, 1993.

Human Photoirritation/Phototoxicity Study; the Procter & Gamble Co.; Aug., 1992–Sep., 1992.

Human Photosensitization Study; the Procter & Gamble Co.; Sep., 1992–Jan., 1993.

Human Facial Moisturizer Split Face Irritation Study; the Procter & Gamble Co.; Nov., 1992.

Randomized, Vehicle–Controlled, Double–Blind Study to Examine Effects of Topically Applied NAC on Photodamaged Wrinkled Human Facial Skin; the Procter & Gamble Co.; Jun., 1993–Dec., 1993.

*Primary Examiner*—Nathan M. Nutter
*Attorney, Agent, or Firm*—Loretta J. Henderson; John M. Howell; David L. Suter

[57] ABSTRACT

The subject invention involves topical depilatory compositions, at a pH of 7 or below, comprising sulfhydryl compounds. The subject invention further relates to methods for removing vellus hair from mammalian skin comprising topical application of a composition, at a pH of 7 or below, comprising a sulfhydryl compound or a cosmetically- and/or pharmaceutically-acceptable salt thereof.

7 Claims, No Drawings

DEPILATORY COMPOSITIONS COMPRISING SULFHYDRYL COMPOUNDS

TECHNICAL FIELD

The subject invention relates to the field of hair removal in mammalian skin. Specifically, the subject invention relates to methods for depilation of vellus hair in human skin.

BACKGROUND

The removal of hair from the human body has received considerable attention, both for medical and for cosmetic reasons. Various methods exist to remove unwanted hair. Conventional methods focus on mechanical removal and chemical depilation, whereby unwanted hair is removed once it has already appeared above the surface of the skin. Other methods involve the prevention, suppression or retardation of hair growth, by an alteration in the rate and character of hair growth.

Mechanical methods employed for depilation include tweezing, plucking, electrolysis, shaving and X-ray techniques. Tweezing and plucking are of limited utility because their use is confined to a localized area. Electrolysis and X-ray techniques are painful and require the use of expensive equipment, while shaving leads to skin irritation.

Chemical depilatory compositions are effective in removing unwanted hair from larger areas on the skin. These compositions typically cleave disulfide bonds in hair keratin, causing the hair fiber to disintegrate. However, most chemical depilatory compositions are strongly alkaline, causing dermal irritation, particularly on sensitive facial skin.

At present, compositions generally called "waxes" are also used for depilation. These are applied to the skin in a molten state. On cooling and hardening, the wax enmeshes the hair it contacts. The wax is thin stripped from the skin, pulling out the enmeshed hair by its roots. Even though waxing is longer-lasting than other chemical methods, it is disfavored because of the tendency to cause irritation, swelling or possible burning.

Of the methods employed to alter the rate and character of hair growth, most involve the application of anti-androgens to control dermatological conditions associated with androgen-dependent disorders, such as female hirsutism. However, these methods have undesirable side effects such as systemic anti-androgen effects, teratogenecity and pituitary dysfunction and are, consequently, of limited use.

For the foregoing reasons, there is a need to develop a method which is efficacious, easily administered, non-irritating, long-lasting, and can remove unwanted hair and/or regulate the growth of unwanted hair without allowing rapid return growth.

It is an object of the subject invention to provide topical compositions for removing unwanted vellus hair from mammalian skin.

It is further object of the subject invention to provide such compositions which are gentler and less irritating to the skin than existing compositions.

It is also an object of the subject invention to provide methods for removing vellus hair from mammalian skin.

SUMMARY OF THE INVENTION

The subject invention involves topical compositions, for removing unwanted hair, especially vellus hair, and/or regulating hair growth in a mammal susceptible to or suffering from hirsutism or unwanted hair, comprising as an active a sulfhydryl compound in a cosmetically- and/or pharmaceutically-acceptable carrier such that the composition has a pH of 7 or below. The subject invention further involves methods of removing unwanted vellus hair and/or regulating hair growth in a mammal susceptible to our suffering from hirsutism or unwanted hair comprising topically applying to the skin of the mammal a "leave-on" composition comprising a sulfhydryl compound in a cosmetically- and/or pharmaceutically-acceptable carrier such that the composition has a pH of 7 or below.

DETAILED DESCRIPTION OF THE INVENTION

As used herein, "sulfhydryl compound" means a compound having an —S—H group selected from the group consisting of thioglycolic add, cysteine, homocysteine, glutathione, thioglycerol, thiomalic acid, 2-mercaptopropionic acid, 3-mercaptopropionic acid, thiodiglycol, 2-mercaptoethanol, dithiothreitol, thioxanthene, thiosalicylic acid, thiolactic acid, thiopropionic acid, thiodiglycolic acid, N-acetyl-L-cysteine, lipoic acid, and cosmetically- and/or pharmaceutically-acceptable salts of any of the foregoing compounds. Mixtures of sulfhydryl compounds are suitable for use herein. Preferred sulfhydryl compounds include thioglycolic acid, cysteine, glutathione, N-acetyl-L-cysteine, lipoic acid, thiosalicylic acid, and thiolactic acid and cosmetically- and/or pharmaceutically-acceptable salts thereof. More preferred sulfhydryl compounds include thioglycolic acid, cysteine, glutathione and N-acetyl-L-cysteine and cosmetically- and/ or pharmaceutically-acceptable salts thereof. The most preferred sulfhydryl compound is N-acetyl-L-cysteine and cosmetically- and/or pharmaceutically-acceptable salts thereof.

As used herein, "cosmetically- and/or pharmaceutically-acceptable salts" of the sulfhydryl compound include, but are not limited to alkali metal salts, e.g., sodium, lithium, rubidium and potassium salts; alkaline earth metal salts, e.g., magnesium, calcium and strontium salts; non-toxic heavy metal salts, e.g., aluminum salts and zinc salts; boron salts; silicon salts; ammonium salts; trialkylammonium salts, e.g., trimethylammonium and triethylammonium; and tetralkylonium salts. Preferred cosmetically- and/or pharmaceutically-acceptable salts of the sulfhydryl compound include $Na^+$, $K^+$, $Ca^{++}$, $Mg^{++}$, $Al_2(OH)_5^+$, $NH_4^+$, $(HOCH_2CH_2)_3NH^+$, $(CH_3CH_2)_3NH^+$, $(CH_3CH_2)_4N^+$, $C_{12}H_{25}(CH_3)_3N^+$ and $C_{12}H_{25}(C_5H_4N)_3N^+$ salts. More preferred salts of the sulfhydryl compound include $Na^+$, $K^+$, $NH_4^+$, and $(HOCH_2CH_2)_3NH^+$ salts. Most preferred salts of the sulfhydryl compound include $Na^+$ and $NH_4^+$ salts. Suitable salts of the sulfhydryl compound are described, for example, in U.S. Pat. No. 5,296,500, issued to Hillebrand on Mar. 22, 1994, incorporated herein by reference.

It has been unexpectedly found that compositions containing sulfhydryl compounds at acidic or neutral pH exhibit the ability to remove unwanted vellus hair in mammalian skin without undesirable side effects, such as skin irritation and odor, commonly associated with known depilatory formulations. While not limited to any particular mode of action it is believed that sulfhydryl compounds remove unwanted vellus hair by breaking the disulfide bonds present in vellus hair keratin. Without intending to be bound or limited by theory, the compositions of this invention may also regulate hair growth.

As used herein, "vellus hair" means a fine, short hair of less than 1 cm in length, containing little or no pigmentation.

The subject compositions depilate vellus hair because the disulfide bonds present in such hair are susceptible to cleavage by sulfhydryls.

As used herein "terminal hair" means a coarse, pigmented, medullated hair which is longer than a vellus hair. Terminal hairs are typically seen on the scalp, eyebrows, and eyelashes, and include secondary sexual hair seen in the pubic region, abdomen, face and axillae. The subject compositions soften terminal hair.

As used herein "leave-on" means a composition that is topically applied without washing off after a given length of time.

As used herein, "topical application" means directly laying on or spreading on the skin of a mammal.

As used herein, "safe and effective amount" means an amount of compound or composition sufficient to significantly induce a positive modification in the condition to be treated, but low enough to avoid serious side effects (at a reasonable benefit/risk ratio), within the scope of sound medical judgment. As may be applicable for certain uses of the present compositions, the safe and effective amount of the compound or composition will vary with the particular condition being treated, the age and physical condition of the patient being treated, the severity of the condition, the duration of the treatment, the nature of concurrent therapy, the specific compound or composition employed, the particular cosmetically- and/or pharmaceutically-acceptable carrier utilized, and like factors within the knowledge and expertise of an attending physician.

As used herein, "cosmetically- and/or pharmaceutically-acceptable" means that salts, drugs, medicaments, inert ingredients or other materials which the phrase describes are suitable for use in contact with the tissues of humans and lower animals without undue toxicity, incompatibility, instability, irritation, allergic responses, and the like, commensurate with a reasonable benefit/risk ratio.

As used herein, "regulating hair growth" means decreasing the rate of hair growth and/or inducing the formation of fewer hair strands, and/or decreasing the diameter of the hair strand, and/or shortening the hair strand and/or preventing, retarding, suppressing or arresting the process of hair growth.

Compositions of this invention preferably comprise from about 0.005% to about 25%, more preferably from about 0.1% to about 15%, still more preferably from about 0.5% to about 10%, yet more preferably from about 1% to about 7%, even more preferably from about 2% to about 5%, most preferably about 2% of the sulfhydryl compound.

The Carrier

The compositions of the present invention comprise a solid, semi-solid or liquid cosmetically acceptable- and/or pharmaceutically-acceptable carrier to enable the sulfhydryl active to be delivered to the desired target at an appropriate concentration. The carrier can itself be inert or it can possess physiological or pharmaceutical benefits of its own. The active is topically applied to the skin of a subject in need of treatment. Topical application is preferably achieved with compositions in the forms of lotions, solutions, ointments, serums, sprays, tonics, creams, bars, cream rinses, gels, sticks, mousses, pastes and the like.

Topical compositions of the present invention can be formulated as liquids, for example, as a lotion, mousse or milk. Such liquid compositions may be formulated for use in conjunction with an applicator such as a roll-ball applicator, a pad applicator, or a spray device such as an aerosol can containing propellant, or a container fitted with a pump to dispense the liquid product, or a liquid-impregnated fabric, such as a tissue wipe.

Alternatively, the compositions of the invention can be solid or semi-solid, for example, sticks, serums, creams or gels. Such solid or semi-solid compositions may be formulated for use in conjunction with a suitable applicator or simply a tube, jar or other convenient container.

The selection of a carrier for this purpose presents a wide range of possibilities depending on the required product form of the composition. Suitable vehicles can be classified as described hereinafter.

The term "topical carrier" refers to substances which can act as diluents, dispersants, or solvents for the sulfhydryl active which therefore ensure that it can be applied to and distributed evenly over the selected target at an appropriate concentration. Topical carders useful in compositions of the subject invention can include water as a vehicle, and one or more cosmetically- and/or pharmaceutically-acceptable vehicles other than water.

The topical carrier is preferably one which can aid and/or enhance penetration of the sulfhydryl active into the skin to reach the immediate environment of the hair follicle. Carders useful in topical compositions according to the invention may include penetration enhancers such as liposomes, latex lattices, microspheres, cyclodextrans and various forms of microencapsulation of the active. A preferred amount of penetration enhancing agent is from about 1% to about 5% of the composition.

Generally, the carrier is either aqueous or organic in nature or an aqueous emulsion, and is capable of having the sulfhydryl active dispersed or dissolved therein. The carrier may include cosmetically- and/or pharmaceutically-acceptable emollients, skin penetration enhancers, coloring agents, fragrances, emulsifiers, thickening agents, and/or solvents.

Topical compositions of the present invention may be formulated as a composition comprising an emollient. Such compositions typically comprise from about 1% to about 50%, preferably from about 5% to about 20% of a topical cosmetically- and/or pharmaceutically-acceptable emollient; and a safe and effective amount of the sulfhydryl active.

As used herein, "emollients" refer to materials used for the prevention or relief of dryness, as well as for the protection of the skin. A wide variety of suitable emollients are known and may be used herein. Such emollients include, but are not limited to, hydrocarbon oils and waxes, silicon oils, triglyceride fats and oils, acetoglyceride esters, ethoxylated glycerides, alkyl esters of fatty acids having 10 to 20 carbon atoms, alkenyl esters of fatty acids having 10 to 20 carbon atoms, fatty acids having 8–22 carbon atoms, fatty alcohols having 8–22 carbon atoms, fatty alcohol ethers, ether-esters, lanolin and derivatives, polyhydric alcohols and their polyether derivatives, wax esters, beeswax derivatives, vegetable waxes, phospholipids, sterols, and amides. SAGARIN, COSMETICS, SCIENCE AND TECHNOLOGY, 2nd Edition, Vol. 1, pp. 32–43 (1972), incorporated herein by reference, contains numerous examples of suitable emollient materials.

Topical compositions of the subject invention may also be formulated as a cream. Preferably the creams of the present invention comprise a safe and effective amount of the sulfhydryl active; from about 5% to about 50%, preferably from about 10% to about 25%, of an emollient; and from about 25% to about 95% water. Optionally the cream form contains a suitable emulsifier. When an emulsifier is included, it is in the composition at a level from about 3% to about 50%, preferably lo from about 5% to about 20%. Emulsifiers may be nonionic, anionic or cationic. Suitable emulsifiers are disclosed in, for example, U.S. Pat No. 3,755,560, issued Aug. 28, 1973, Dickert et al.; U.S. Pat. No. 4,421,769, issued Dec. 20, 1983, Dixon et al.; and McCutcheon's *Detergents and Emulsifiers*, North American Edition, pp. 317–324 (1986); the disclosures of which are incorporated herein by reference. Preferred emulsifiers are anionic or nonionic.

Topical compositions of the subject invention may also be formulated as a composition comprising a lotion. Preferably the lotions of the subject invention comprise a safe and effective about of the sulfhydryl active; from about 1% to about 50%, preferably from about 3% to about 15% of an emollient; and from about 45% to about 85%, preferably from about 50% to about 75% water. Optionally, the lotion form may contain a suitable emulsifier, comprising from about 3% to about 50%, preferably from about 10% about 20% of the composition. Example of suitable emulsifiers are included herein above in the disclosure of cream formulations.

Preferably a solution form of the present invention comprises a safe and effective amount of the sulfhydryl active, water and a suitable organic solvent. Suitable organic materials useful as the solvent or a part of a solvent system are as follows: propylene glycol, glycerin, polyethylene glycol (M.W. 200-600), polypropylene glycol (M.W. 425-2025), sorbitol esters, 1,2,6-hexanetriol, ethanol, isopropanol, diethyl tartrate, butanediol, and mixtures thereof.

Gel compositions of the present invention can be formulated by simply mixing a suitable thickening agent to the previously described solution compositions. The gel compositions preferably comprise a safe and effective amount of the sulfhydryl active; from about 5% to about 75%, preferably from about 10% to about 50%, of an organic solvent as previously described for solutions; and from about 0.5% to about 20%, preferably from about 1% to about 10% of the thickening agent.

Compositions of solid forms of the present invention have use as stick-type compositions intended for application to the body. Such compositions preferably comprise a safe and effective amount of the sulfhydryl active, and from about 50% to about 98%, preferably from about 60% to about 90%, of the previously described emollients. Such compositions can further comprise from about 1% to about 20%, preferably from about 5% to about 15%, of a suitable thickening agent, and optionally emulsifiers and water, The preferred lotions, solutions, sticks, gels, and creams more preferably also contain a preservative, preservative enhancer, zinc, and/or a zinc salt as described herein. These agents may be incorporated into the aforementioned formulations in the amounts described herein.

The compositions of the present invention are preferably formulated to have a pH of 7 or below. The pH values of these compositions preferably range from about 2 to about 7, more preferably from about 3 to about 6, most preferably from about 4.5 to about 5.5. Compositions having a pH within the range of about 4.5 to 7 tend to exhibit less skin irritation, less odor, and greater shelf stability relative to corresponding compositions having a pH of greater than about 8.5.

Other Ingredients

The compositions of this invention may contain other ingredients, including but not limited to preservatives, preservative enhancers, and actives in addition to the sulfhydryl active. However, certain agents may decrease the activity of the sulfhydryl compound, particularly N-acetyl-L-cysteine, in topical formulations. First, an excessive number of microbial agents may decrease the activity of the sulfhydryl compound, for example by microbial metabolism of the compound. Second, it has been found that formaldehyde may chemically react with the sulfhydryl compound to decrease its activity. Thus, when a composition containing the sulfhydryl compound is formulated with a formaldehyde or a formaldehyde forming preservative or other material, the composition may have decreased activity of the sulfhydryl compound over time relative to the corresponding formulation that does not contain formaldehyde or a compound capable of forming formaldehyde. Therefore, it is desirable to provide compositions containing sulfhydryl compounds that have preservative efficacy and which do not include formaldehyde or formaldehyde forming preservatives or other materials.

The compositions are therefore preferably substantially free of formaldehyde and materials that may form or release formaldehyde when present in the composition, including preservatives that may form or release formaldehyde in the composition. Formaldehyde and materials that may form or release formaldehyde in the composition are alternatively referred to herein as "formaldehyde donor(s)." As used herein, "substantially free of formaldehyde donors" means that there are no detectable formaldehyde donors, preferably no formaldehyde donors. The presence of formaldehyde donors may be indicated by the presence of formaldehyde in the composition by any suitable analytical technique, for example high pressure liquid chromatography. The presence of such donors may be detected initially or evidenced by the generation of formaldehyde over time.

The topical compositions of the invention preferably comprise one or more preservatives. Preferred preservatives are those which are substantially free of formaldehyde donors. Thus, the preservatives preferred for use herein are those that do not form or release formaldehyde in the composition either in the process of preserving or in an unrelated process. In contrast, formaldehyde forming or releasing preservatives form or release formaldehyde in the composition either in the process of preserving or in an unrelated process.

More preferred preservatives include benzyl alcohol, propylparaben, ethylparaben, butylparaben, methylparaben, benzylparatien, isobutylparaben, phenoxyethanol, ethanol, sorbic acid, benzoic acid, methylchloroisothiazolinone, methylisothiazolinone (a preservative containing a mixture of methylchloroisothiazolinone and methylisothiazolinone being commercially available, for example, from Rohm & Haas as Kathon CC®), methyl dibromoglutaronitdle (commercially available, for example, from Calgon as Tektamer 38®), dehydroacetic acid, o-phenylphenol, sodium bisulfite, dichlorophen, salts of any of the foregoing compounds, and mixtures of any of the foregoing compounds.

Even more preferred preservatives are selected from the group consisting of benzyl alcohol, propylparaben, methylparaben, phenoxyethanol, methylchloroisothiazolinone, methylisothiazolinone, benzoic acid, salts of any of the foregoing preservatives, and mixtures of any of the foregoing compounds.

Still more preferred preservatives are benzyl alcohol, propylparaben, methylparaben, phenoxyethanol and mixtures thereof. Yet even more preferably, the preservative is a mixture of propylparaben and methyl paraben with either or both of benzyl alcohol and phenoxyethanol. In addition to stability of the sulfhydryl compound, these mixtures provide broad preservative efficacy with no or only minimal risk of skin irritation to the user. Most preferably, the preservative is a mixture of benzyl alcohol, propylparaben and methylparaben. In addition to stability of the sulfhydryl compound and broad preservative efficacy, this mixture presents a particularly low risk of skin irritation to the user.

The use of the foregoing preservatives that are substantially free of formaldehyde donors is described in more detail in the copending U.S. patent application entitled "Topical Compositions Comprising N-Acetyl-L-Cysteine," filed on Jun. 7, 1995 in the names of Greg. G. Hillebrand and Marcia S. Schnicker, which is incorporated herein by reference in its entirety. The foregoing preservatives are preferably used in the compositions of this invention in the same amounts as described for the compositions of the just referenced patent application.

The compositions of this invention preferably comprise a safe and effective amount of a preservative enhancer. As used herein, the term "preservative enhancer" means an agent whose purpose is to enhance the activity of the preservative. As will be understood by the artisan having ordinary skill, the preservative enhancer does not itself typically provide sufficient efficacy; it tends to increase the efficacy of the preservative. Enhancement of the preservative efficacy may involve chelation. Preferred preservative enhancers useful in the present invention include ethylenediaminetetraacetic acid (EDTA), butylene glycol, propylene glycol, ethanol, and mixtures thereof. Where the preservative includes a paraben, e.g., methyl or propyl paraben, EDTA is the preferred preservative enhancer. The use of such enhancers is described in more detail in the above-referenced and incorporated copending U.S. patent application entitled "Topical Compositions Comprising N-Acetyl-L-Cysteine," filed on Jun. 7, 1995 in the names of Greg. G. Hillebrand and Marcia S. Schnicker. The preservative enhancers are preferably used in the compositions of this invention in the same amounts as described for the compositions of the just referenced patent application.

The compositions of the invention preferably contain zinc or a zinc salt which may complex with the sulfhydryl compound. Without being bound by theory, the zinc most likely removes odor by complexing with malodorous $H_2S$ which may be formed in trace amounts as the sulfhydryl compound decomposes. The zinc may additionally or alternatively increase the stability of the sulfhydryl compound. The use of zinc salts in a manner which is suitable for the present invention is further described in U.S. Pat. No. 5,296,500, Hillebrand, issued on Mar. 22, 1994, which is incorporated herein by reference.

The compositions of the subject invention may optionally comprise other actives capable of functioning in different ways to enhance the benefits of the sulfhydryl active (thus, the other actives should not significantly reduce the activity of the sulfhydryl compound). Examples of such substances include, but are not limited to anti-inflammatory agents, anti-androgens, depilatories/hair growth suppressants, sunscreens, sunblocks, and moisturizers.

A. Anti-Inflammatories

An anti-inflammatory agent may be included as an active in the subject invention, preferably from about 0.1% to about 10%, more preferably from about 0.5% to about 5% of the composition. The exact amount of anti-inflammatory agent to be used in the composition will depend on the particular anti-inflammatory agent utilized since such agents vary widely in potency. Suitable anti-inflammatory agents include steroidal anti-inflammatories, such as hydrocortisone, alpha-methyl dexamethasone, beclomethasone dipropionate, and amcinafel; nonsteroidal anti-inflammatories, such as oxicams, salicylates, acetic acid derivatives, fenamates, pyrazoles and propionic acid derivatives; as well as "natural" anti-inflammatories, such as candelilla wax, alpha bisabolol, aloe vera, Manjistha (extracted from plants in the genus Rubia), and Guggal, (extracted from plants in the genus Commiphora).

B. Anti-androgens

In a preferred composition useful in the subject invention, an anti-androgen is included as an active along with the active. As used herein "anti-androgen" means a compound capable of correcting androgen-related disorders by interfering with the action of androgens at their target organs. The target organ for the subject invention is mammalian skin.

A safe and effective amount of an anti-androgen may be added to the compositions useful in the subject invention, preferably from about 0.001% to about 1%, more preferably from about 0.01% to about 0.1%.

Anti-androgens which are androgen receptor antagonists as well as anti-androgens which are 5-α reductase inhibitors are useful in the compositions of the subject invention. Examples of such anti-androgens are more fully disclosed in U.S. Pat. No. 4,888,336, Holt, Metcalf and Levy, issued Dec. 19, 1989; U.S. Pat. No. 5,110,939, Holt, Metcalf and Levy, issued May 5, 1992; U.S. Pat. No. 5,120,742, Rasmusson and Reynolds, issued Jun. 9, 1992, and U.S. Pat. No. 4,859,681, Rasmusson and Reynolds, issued Aug. 22, 1989; all incorporated herein by reference. See also Stewart, M., and P. Pochi, "Anti-androgens and the Skin", *International Society of Tropical Dermatology*, Vol. 17, No. 3, pp 167–179 (1978); incorporated herein by reference.

Preferred anti-androgens useful in compositions of the subject invention are cyproterone acetate, finasteride, chlormadinone acetate, 17-α propylmesterolone, 17-α estradiol acetate, dienoestrol diacetate, estradiol benzoate, inocoterone acetate, spironolactone, 11-α hydroxyprogesterone and cyproterone acetate thioacetate.

C. Depilatories/Hair Growth Suppressants

In a preferred composition useful in the subject invention, a depilatory or hair growth suppressant is included as an active along with the active. As used herein, "depilatory" means an agent capable of removing hair from the skin by cleaving the disulfide bonds in hair keratin, thereby causing the hair fiber to disintegrate. A safe and effective amount of depilatory agent may be added to the compositions useful in the subject invention, preferably from about 0.001% to about 1%, more preferably from about 0.05% to about 0.5%.

Preferred depilatories useful in the subject invention include ammonium thioglycolate, barium sulfate, calcium thioglycolate, ethanolamine thioglycolate, potassium thioglycolate, sodium thioglycolate, thioglycolic acid and thioacetic acid.

As used herein "hair growth suppressant" means an agent capable of retarding the growth of hair. A preferred hair growth suppressant useful in the subject invention is diethyldithiocarbamic acid.

D. Sunscreens and Sunblocks

A sunscreen or sunblock is included as an active along with the actives of the subject invention in preferred compositions of the subject invention. A wide variety of conventional sunscreening agents are suitable for use in combination with the desquamation agents. Sagarin, et al., at Chapter VIII, pages 189 et seq., of *Cosmetics Science and*

*Technology*, disclose numerous suitable agents, incorporated herein by reference. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, octyl, benzyl, menthyl, glyceryl, and dipropyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylacetoumbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxynaphthoic acid and its salts; o- and p-Hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives (e.g., hexaethylether); Coutyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-iso-propyldibenzoylmethane; butylmethoxydibenzoylmethane; etocrylene; [3-(4'-methylbenzylidene bornan-2-one) and 4-isopropyl-di-benzoylmethane.

Of these, 2-ethylhexyl-p-methoxycinnamate, 4,4'-t-butyl methoxydibenzoylmethane, 2-hydroxy-4-methoxybenzophenone, octyl-dimethyl-p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethyl-aminobenzoic acid or aminobenzoate, 2-ethylhexyl-p-dimethylamino-benzoate, 2-phenylbenzimidazole-5-sulfonic acid, 2-(p-dimethylaminophenyl)-5-sulfonicbenzoxazoic acid and mixtures of these compounds, are preferred.

More preferred sunscreens useful in the compositions useful in the subject invention are 2-ethylhexyl-p-methoxycinnamate, butylmethoxydibenzoylmethane, 2-hydroxy-4-methoxybenzophenone, octyldimethyl-p-aminobenzoic acid and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl) methylaminobenzoic acid ester with 4-hydroxydibenzoylmethane; 4-N,N-(2-ethylhexyl) methylaminobenzoic acid ester of 2-hydroxy-4-(2-hydroxyethoxy)benzophenone; 4-N,N-(2-ethylhexyl)-methylaminobenzoic acid ester of 4-(2-hydroxyethoxy) dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

A safe and effective amount of sunscreen may be used as an added active in compositions useful in the subject invention. The sunscreening agent must be compatible with the sulfhydryl active. The composition preferably comprises from about 1% to about 20%, more preferably from about 2% to about 10%, of a sunscreening agent. Exact amounts will vary depending upon the sunscreen chosen and the desired Sun Protection Factor (SPF).

An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

E. Moisturizers

In a preferred composition useful in the subject invention, a moisturizer is included as an active along with the sulfhydryl active. Preferred moisturizers useful in the subject invention include glycerol, mineral oil, petrolatum, isopropyl myristate and hyaluronic acid. More preferred moisturizers include glycerol and petrolatum.

The compositions of the present invention are generally prepared by conventional methods such as are known in the art of making topical compositions. Such methods typically involve mixing of the ingredients to a relatively uniform state, with or without heating, cooling, application of vacuum, and the like.

For optimum stability of the sulfhydryl compound, the compositions of this invention should be manufactured, packaged and stored in a manner which avoids simple air oxidation of the sulfhydryl compound, which is well known in the art. Thus, exposure of the compositions to air during manufacture, packaging and storage should be minimized.

Delivery Methods for Topical Compositions

The topical compositions useful for the methods of the subject invention can be delivered from a variety of delivery devices. The following are two non-limiting examples:

A. Medicated Cleansing Pads

The compositions useful herein can be incorporated into a medicated pad. Preferably these pads comprise from about 50% to about 75% by weight of one or more layers of nonwoven fabric material and from about 20% to about 50% by weight of a liquid composition deliverable from the nonwoven fabric material preferably comprising from about 0.01% to about 20% the active, more preferably from about 1% to about 10%, more preferably still from about 2% to about 7%, also preferably 5% the active. These pads are described in detail in U.S. Pat. No. 4,891,228, issued to Thaman et al., Jan. 2, 1990; and U.S. Pat. No. 4,891,227, issued to Thaman et al., Jan. 2, 1990; both of which are incorporated by reference.

B. Dispensing Devices

The compositions useful herein can also be incorporated into and delivered from a soft tipped or flexible dispensing device. These devices are useful for the controlled delivery of the compositions to the skin surface and have the advantage that the treatment composition itself never need be directly handled by the user. Non-limiting examples of these devices comprise a fluid container including a mouth, an applicator, means for holding the applicator in the mouth of the container, and a normally closed pressure responsive valve for permitting the flow of fluid from the container to the applicator upon the application of pressure to the valve.

The valve can include a diaphragm formed from an elastically fluid-impermeable material with a plurality of non-intersecting arcuate slits therein, where each slit has a base which is intersected by at least one other slit, and where each slit is out of intersecting relation with its own base, and wherein there is a means for disposing the valve in the container inside of the applicator. Examples of these applicator devices are described in U.S. Pat. No. 4,693,623, to Schwartzman, issued Sep. 15, 1987; U.S. Pat. No. 4,620,648, to Schwartzman, issued Sep. 15, 1987; U.S. Pat. No. 3,669,323, to Harker et al., issued Jun. 13, 1972; U.S. Pat. No. 3,418,055, to Schwartzman, issued Dec. 24, 1968; and U.S. Pat. No. 3,410,645, to Schwartzman, issued Nov. 12, 1968; all of which are incorporated herein by reference. Examples of applicators useful herein are commercially available from Dab-O-Matic, Mount Vernon, N.Y.

Methods of Application

The subject compositions are useful in removing unwanted vellus hair, and/or regulating hair growth, and/or softening terminal hair.

A preferred method of applying the subject compositions involves multiple topical application to the face, underarm, legs and other areas where unwanted hair is likely to grow. Once applied, the composition is left on. The amount of the composition and the frequency of application can vary widely, depending on the area in questions, the desired effect and/or personal needs, but it is suggested as an example that topical application preferably range from about five times daily, to once every other day, more preferably from about three times daily to once daily, and most preferably about twice daily. The composition for topical application will preferably contain from about 0.001 to about 50 mg of the active per $cm^2$ skin receiving the topical composition, more preferably from about 0.01 to about 30 $mg/cm^2$, more preferably still from about 0.05 to about 10 $mg/cm^2$, also preferably from about 0.1 to about 2$mg/cm^2$. The period of topical application should be as is needed by the individual, and may be over the subject's adult life, for continued regulation of hair growth and/or removal of unwanted vellus hair.

EXAMPLES

The composition embodiments of the present invention are illustrated in the following non-limiting examples. All parts, percentages, and ratios used herein are by weight unless otherwise specified.

Example I

A topical composition is prepared by combining the following components utilizing conventional mixing techniques and the pH is adjusted to 6.0 by adding NaOH.

| Component | % by weight |
| --- | --- |
| N-acetyl-L-cysteine | 5.0 |
| Propylene glycol | 45.0 |
| Ethanol | 30.0 |
| Water | 20.0 |

1000 mg of the composition per 100 $cm^2$ skin is topically applied to the face twice per day to remove unwanted vellus hair.

Example II

A topical composition is prepared by combining the following components utilizing conventional mixing techniques and the pH is adjusted to 4.5 by adding NaOH.

| Component | % by weight |
| --- | --- |
| Thioglycolic acid | 2.0 |
| Propylene glycol | 57.0 |
| Ethanol | 20.0 |
| Water | 10.0 |
| Benzyl alcohol | 4.0 |
| Glycerin | 5.0 |
| Myristyl alcohol | 2.0 |

4000 mg of the composition per 100 $cm^2$ skin is topically applied once a day to the legs to soften terminal hair.

Example III

A topical composition is prepared by combining the following components utilizing conventional mixing techniques and the pH is adjusted to about 3.0 by adding NaOH.

| Component | % by weight |
| --- | --- |
| Glutathione | 1.0 |
| Propylene glycol | 30.0 |
| Glycerin | 3.0 |
| Water | 66.0 |

2000 mg of the composition per 100 $cm^2$ skin is topically applied twice per day to the face to remove unwanted vellus hair.

Example IV

A topical composition is prepared by combining the following components utilizing conventional mixing techniques and the pH is adjusted to 5.0 by adding NaOH.

| Component | % by weight |
| --- | --- |
| N-acetyl-L-cysteine | 0.5 |
| Propylene glycol | 30.0 |
| Propylene glycol laurate | 1.0 |
| Isopropanol | 20.0 |
| Water | 48.5 |

500 mg of the composition per 100 $cm^2$ skin is topically applied once per day to the face to remove unwanted vellus hair.

Example V

A lotion is prepared by combining the following components utilizing conventional mixing techniques and the pH is adjusted to 4.0 by adding NaOH.

| Component | % by weight |
| --- | --- |
| Cysteine | 5.0 |
| Di-partially hydrogenated tallow dimethyl ammonium chloride | 4.0 |
| Cetyltrimethyl ammonium chloride | 2.0 |
| DC-200 fluid (12500 csk)* | 1.0 |
| Citric acid | 3.5 |
| Ethylene glycol distearate | 1.5 |
| PEG-3 $C_{12}$ alkyl amide | 3.0 |
| Water | 80.0 |

*Dimethylpolysiloxane available from by Dow Chemical Co.

100 mg of the composition per 100 $cm^2$ skin is topically applied to the face three times a day to remove unwanted vellus hair.

Examples VI–VIII

Lotions are prepared, containing the following compositions, using conventional mixing techniques and the pH adjusted to 4.5 by adding NaOH.

| | Example No. | | |
| --- | --- | --- | --- |
| | VI | VII | VIII |
| Component | % by weight | % by weight | % by weight |
| N-acetyl-L-cysteine | 0.1 | 0.5 | 2.0 |
| Hydroxyethyl cellulose | 0.4 | — | 0.4 |
| Absolute ethanol | 15.0 | 15.0 | 15.0 |
| Propane-1,2-diol | — | — | 30.6 |
| Butane-1,3-diol | 33.4 | 33.4 | — |
| Paramethyl benzoate | 0.2 | 0.2 | 0.2 |
| Perfume | 0.5 | 0.5 | 0.5 |
| Water | 50.4 | 50.4 | 48.7 |

Use of an amount of any of the above compositions to deposit about 750 mg per 100 $cm^2$ of the composition to the underarm area once a day is appropriate after initial removal by shaving. Replacement hair is softer than the hair removed.

Example IX

A water-in-oil emulsion is prepared by combining the following ingredients, using conventional mixing techniques and the pH is adjusted to 6.5 by adding NaOH.

| Component | % by weight |
| --- | --- |
| Oily Phase | |
| Lipoic acid | 5.0 |
| Cetearyl alcohol | 5.0 |
| Silicon oil, 200 fluid | 1.0 |
| Isopropyl myristate | 2.0 |
| Sodium stearoyl-2-lactylate | 2.0 |
| Aqueous Phase | |
| Propylene glycol | 5.0 |
| Sodium citrate | 0.2 |
| Perfume | 0.1 |
| Water | 79.7 |

The emulsion is prepared by taking 10 parts of the oily phase and adding it slowly with stirring to 90 parts by volume of the aqueous phase. Use of an amount of the emulsion to deposit about 1000 mg per 100 $cm^2$ of the emulsion three times a day to the legs is appropriate, after initial hair is removed by shaving. Replacement terminal hair is softer than the hair removed.

Example X

An oil-in-water cream is prepared by mixing the following components and the pH is adjusted to 3.5 by adding NaOH.

| Component | % by weight |
| --- | --- |
| Oily Phase | |
| N-acetyl-L-cysteine | 5.0 |
| Sorbitan monoleate | 20.0 |
| Quaternium-18-hectonite | 5.0 |
| Liquid paraffin | 60.0 |
| Aqueous Phase | |
| Xanthan gum | 1.0 |
| Preservative | 0.3 |
| Perfume | 0.2 |
| Water | 8.5 |

The cream is prepared by mixing the oily phase and heating to 65° C. The aqueous phase is combined and heated to 70° C. The aqueous phase is added to the oil phase with suitable agitation. Moderate agitation is applied while cooling. About 5 mg of the cream is deposited per 100 $cm^2$ on the face once a day to remove unwanted vellus hair.

Example XI

Prepare an oil-in-water cream by mixing the following components and adjusting the pH to 4.5. Prepare the cream as described for Example X.

| Component | % by weight |
| --- | --- |
| Oil Phase | |
| Perfume | 0.20 |
| Cetyl alcohol, NF | 1.00 |
| Stearyl alcohol, NF | 1.00 |
| Polyoxyethylene (50:50 - 12/20) cetyl/stear (50:50) | 1.00 |
| Propylene glycol dicaprylate/dicaprate | 3.00 |
| Glycerol monostearate | 2.00 |
| Glyceryl monostearate-palmitate | 2.00 |
| Water Phase | |
| N-acetyl-L-cysteine | 5.25 |
| Distilled Water | 77.19 |
| Glycerin | 3.00 |
| Citric acid | 0.50 |
| Benzyl alcohol | 0.50 |
| Propylparaben | 0.1 |
| Methylparaben, NF | 0.25 |
| Zinc oxide, USP | 0.26 |
| Butylene glycol | 1.50 |

| Component | % by weight |
| --- | --- |
| Sodium hydroxide | 1.12 |
| disodium EDTA | 0.13 |

About 5 mg of the cream is deposited per 100 cm$^2$ on the face once a day to remove unwanted vellus hair.

The cream exhibits enhanced shelf stability, particularly of the N-acetyl-L-cysteine, relative to a corresponding composition which contains a formaldehyde donor such as a preservative which forms or releases formaldehyde in the composition as part of the preservation or another process. Thus, the cream exhibits enhanced N-acetyl-L-cysteine efficacy, relative to the same corresponding composition.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

What is claimed is:

1. A method of removing unwanted vellus facial hair in mammals comprising topically applying to the face of a mammal in need of treatment a composition comprising:

a) a safe and effective amount of a sulfhydryl compound selected from the group consisting of cysteine, homocysteine, glutathione, thioglycerol, thiomalic acid, 2-mercaptopropionic acid, 3-mercaptopropionic acid, 2-mercaptoethanol, dithiothreitol, thiosalicylic acid, N-acetyl-L-cysteine, and cosmetically- and/or pharmaceutically-acceptable salts thereof, and b) a safe and effective amount of a topical carrier, the composition having a pH of 7 or below.

2. The method of claim 1 wherein said composition is applied from about five times a day to about once every other day.

3. The method of claim 2 wherein:

a) said sulfhydryl compound is selected from the group consisting of cysteine, glutathione, N-acetyl-L-cysteine, thiosalicylic acid, 2-mercaptopropionic acid, and cosmetically- and/or pharmaceutically-acceptable salts thereof; and b) the amount of said sulfhydryl compound applied to the skin is from about 0.01 mg per cm$^2$ skin to about 30 mg per cm$^2$ skin.

4. The method of claim 3 wherein:

a) said sulfhydryl compound is N-acetyl-L-cysteine or a cosmetically- and/or pharmaceutically-acceptable salt thereof, b) said composition has a pH ranging from about 3 to about 6; and c) said composition is applied from about three times a day to about once a day.

5. The method of claim 4 wherein said amount of sulfhydryl compound applied to the skin ranges from about 0.05 mg per cm$^2$ skin to about 10 mg per cm$^2$ skin.

6. The method of claim 1 wherein the sulfhydryl compound is selected from N-acetyl-L-cysteine and cosmetically- and/or pharmaceutically-acceptable salts thereof.

7. The method of claim 1 wherein the pH of said composition is 6 or below.

* * * * *